(12) United States Patent
de Juan, Jr. et al.

(10) Patent No.: US 7,137,994 B2
(45) Date of Patent: Nov. 21, 2006

(54) INJECTABLE BAG INTRAOCULAR LENS SYSTEM, INSERTING DEVICE FOR USE THEREWITH, METHOD FOR INSERTING AN INJECTABLE BAG INTRAOCULAR LENS WITHIN A HUMAN EYE, METHODS FOR TREATING APHAKIA AND SYSTEM KITS

(75) Inventors: Eugene de Juan, Jr., La Canada, CA (US); Eric T. Lee, San Francisco, CA (US)

(73) Assignee: John Hopkins University, Baltimore, MD (US)

( * ) Notice: Subject to any disclaimer, the term of this patent is extended or adjusted under 35 U.S.C. 154(b) by 0 days.

(21) Appl. No.: 09/904,201

(22) Filed: Jul. 11, 2001

(65) Prior Publication Data

US 2002/0055776 A1 May 9, 2002

Related U.S. Application Data

(60) Provisional application No. 60/217,466, filed on Jul. 11, 2000.

(51) Int. Cl.
*A61F 2/16* (2006.01)
(52) U.S. Cl. ............ 623/6.12; 623/6.13; 606/107
(58) Field of Classification Search ............ 623/6.12, 623/6.13; 606/107, 194, 192
See application file for complete search history.

(56) References Cited

U.S. PATENT DOCUMENTS

| | | | | |
|---|---|---|---|---|
| 4,253,199 A | * | 3/1981 | Banko | 623/6.13 |
| 4,685,921 A | | 8/1987 | Peyman | |
| 4,693,717 A | * | 9/1987 | Michelson | 623/6.13 |
| 4,822,360 A | * | 4/1989 | Deacon | 606/107 |
| 4,836,202 A | * | 6/1989 | Krasner | 606/107 |
| 4,883,485 A | * | 11/1989 | Patel | 623/6.13 |
| 4,995,880 A | * | 2/1991 | Galib | 623/6.13 |
| 5,035,710 A | * | 7/1991 | Nakada et al. | 623/613 |
| 5,066,301 A | * | 11/1991 | Wiley | 623/6.13 |
| 5,213,579 A | * | 5/1993 | Yamada et al. | 623/6.13 |
| 5,702,441 A | * | 12/1997 | Zhou | 606/107 |
| 5,919,145 A | * | 7/1999 | Sahatjian | 606/194 |
| 6,048,364 A | | 4/2000 | Skottun | |
| 6,413,262 B1 | * | 7/2002 | Saishin et al. | 606/107 |

* cited by examiner

*Primary Examiner*—Danton DeMille
(74) *Attorney, Agent, or Firm*—Edwards Angell Palmer & Dodge LLP; Peter F. Corless; Lisa Swiszcz Hazzard

(57) ABSTRACT

Featured is an injectable intraocular lens system including an insertion and injection device and an injectable intraocular lens. In its broadest aspects, the injectable intraocular lens is a deflated flexible bag that is disposed within the insertion and injection device prior to insertion into the eye. In use a portion of the insertion and injection device is inserted into the eye and the flexible bag is deployed out from an aperture in the inserted portion into the eye. Following deployment, the insertion and injection device injects an optical medium, such as a liquid, into the interior of the flexible bag, thereby inflating the bag. In an illustrative embodiment, the amount of medium being injected is selected so that the inflated bag provides the desired corrective power to the intraocular lens so formed. Following injection of the medium, the interconnection between the insertion and injection device and the interior of the flexible bag is broken and a seal is formed so as to keep the medium within the flexible bag interior.

21 Claims, 3 Drawing Sheets

INJECTABLE BAG INTRAOCULAR LENS SYSTEM, INSERTING DEVICE FOR USE THEREWITH, METHOD FOR INSERTING AN INJECTABLE BAG INTRAOCULAR LENS WITHIN A HUMAN EYE, METHODS FOR TREATING APHAKIA AND SYSTEM KITS

This application claims the benefit of U.S. Provisional Application Ser. No. 60/217,466 filed Jul. 11, 2000, the teachings of which are incorporated herein by reference.

FIELD OF INVENTION

The present invention relates generally to systems, devices, and methods for implanting an intraocular lens within an eye in conjunction with the removal of the natural lens as well as methods for treating aphakia and more particularly to such systems, devices and methods for implanting an intraocular lens which is inflated following insertion by injection of a fluid or other flowable material.

BACKGROUND OF THE INVENTION

Cataract is a common ailment effecting the human eyes, especially the eyes of older people, and can lead to blindness. Removal of the clouded biological lens material (i.e., the natural lens) from the capsule of the lens of the affected eye will restore light perception (see also FIG. 1). Full rehabilitation, however, requires that the refractive power of the natural lens be replaced by some other means because the light rays no longer are focused on the retina when the natural lens is removed. Consequently, cataract extraction is a common ophthalmic surgical procedure performed in the United States in which the natural lenses is replaced with a prosthetic optical device such as corrective eye glasses, contact lens and/or intraocular lens, so useful vision can be restored to the operated eye.

In the somewhat distant past, the replacement of the refractive power of the natural lens was achieved by the use of corrective eyeglasses or contact lens. The eyeglasses and contacts, however, have limitations in such an application. Corrective eyeglasses, however, being located in front of the normal position of the human lens, can produce magnification that distorts the shape of viewed objects. Contact lenses cause less magnification and distortion, however, very old and very young patients frequently find handling and wearing these small lenses difficult.

As a result of these limitations, the treatment of cataracts has developed to include the implantation of an artificial lens, typically called an intraocular lens, in the eye to mimic the function of the original natural lens. With implanted intraocular lenses, there is little or no magnification or distortion. Also, there is no need to remove the intraocular lens from the eye or otherwise handle the lens. Generally, intraocular lenses provide good visual acuity at all times, even at night.

Intraocular lenses have definite advantages in terms of vision and convenience over the other methods of aphakic correction. Intraocular lens implantation surgery, however, is more traumatic than simple cataract extraction alone. The additional handling of the cornea and manipulation inside the anterior chamber during lens implantation add to the amount of trauma to the eye. Extreme care must be exercise to limit trauma to the cornea, structures of the anterior chamber, and other structures. In this microfine surgery uncommon agility on the part of even a skilled surgeon often is required. Space limitations in the eye, the required size of the lens once implanted, and considerable manipulations of the lenses during implantation by the surgeon can result in traumatic damage to the corneal endothelium and very often rupture of the posterior capsule by the novice. Damage to the corneal endothelium and rupture of the posterior capsule are complications considered serious.

Initially, the intraocular lens was a relatively rigid lens requiring a 7–8 mm incision to be made in the conjunctiva and sclera just outside the cornea so that the patient's lens can be removed and replaced with an implant intraocular lens. Incision length is dictated more by the size of the intraocular lens to be implanted than by the requirement of removing the patient's natural lens. For example, since the development of the phacoemulsification technique, the patient's natural lens can be removed using an ultrasonic instrument that requires a corneal incision of about 2–3 mm which is much smaller than is needed to insert a rigid intraocular lens.

Efforts to minimize overall intraocular lens size of the rigid lens, and hence reduce trauma, have concentrated on collapsing or folding haptic prior to insertion. Haptics, also called loops or feet, emanate from the lenses and are intended to support and fix the intraocular lens in the eye. Some attempts have been made to reduce the size of the central lenticular portion of intraocular lenses prior to insertion. Silicon lenses which can be folded and gel-type lenses which absorb intraocular fluid and subsequently expand do address the surgical trauma problem. Nevertheless, the incision required for these lenses, although less than the 7–8 mm length for solid intraocular lenses, is relatively large, about 4 mm in length.

A major concern of ophthalmic surgeons is choosing the correct refractive power for lenses. Patients risk additional surgery for lens removal and replacement if the choice of lens refractive power is too much in error. A risk commonly shared in the use of solid, silicon, and gel-type lenses is additional surgery since it is the only alternative for changing a refractive power too much in error. This concern about additional surgery and selecting refractive power becomes of particular concern when dealing with young patients because a rigid lens of the correct refractive power when implanted may not later correctly focus light entering the eye and passing to the retina due to the changing in the size and shape of the eyeball in very young patients as they mature.

As a result, other types of intraocular lens and delivery systems have been developed in which the lens is inserted into the eye in a deflated condition and following such insertion the lens is then inflated or expanded by injecting a liquid, gas or other material into a cavity within the lens. With these other types of intraocular lens, the lens is disposed at least in major part within some sort of insertion device and is forced out of the insertion device using a fluid or rigid member that essentially pushes or ejects the lens from the insertion device.

Also, with these types of intraocular lens one or more separate conduits, cannulas or tubules are provided that interconnects the interior cavity to an external source of the liquid, gas or other material to be injected. Thus, following, such ejection of the lens from the insertion device, the lens is inflated or expanded by flowing the liquid, gas or other material through the one or more conduits or tubules into the cavity. After inflation is completed, the connection with the external source is broken and the surgeon pushes the conduit (s) or tubule(s) attached to the lens into a portion of the eye in which the lens is located. It also must be located so that it does not occlude visual acuity. While such lens and delivery systems have been developed for purposes of reducing the size of the incision required for insertion of the lens, there have arisen complex lens folding issues and haptic breakage concerns. Illustration and description of such lens and/or delivery systems can be found in U.S. Pat. Nos. 4,822,360; 4,693,717; 4,685,921; 4,619,662; 4,585,457 and 4,373,218.

It thus would be desirable to provide a new and novel intraocular lens system as well as related devices and intraocular lens, so as to minimize haptic breakage and concerns with lens manipulation within the lens capsule. It would be particularly desirable to provide such systems, devices, lens and methods related thereto whereby such insertion can be achieved while using minimally sized incisions as in comparison to that for prior art techniques and lens. It also would be desirable to provide such a lens that provides a mechanism for selectively adjusting the refractive power of the lens by means of regulating the material being injected. It also would be yet more desirable to provide such a lens whereby the refractive power can be adjusted following implantation at a later time during the life of the patient to compensate for changing conditions of the eye. Such lens, insertion devices and systems preferably would be simple in construction than prior art devices, lens and systems and such methods would not be unduly complex as compared to prior art methods.

SUMMARY OF THE INVENTION

The present invention features an injectable intraocular lens system including an insertion and injection device and an injectable intraocular lens. In its broadest aspects, the injectable intraocular lens of the present invention includes a flexible bag that is deflated and disposed within the insertion and injection device prior to insertion into the eye. In use a portion of the insertion and injection device is inserted into the eye and the flexible bag is deployed within the eye out from an aperture in the inserted portion. Following deployment, the insertion and injection device injects an essentially optically pure medium, such as a liquid, into the interior of the flexible bag, thereby inflating the bag. In an illustrative embodiment, the amount of medium being injected is selected so that the inflated bag provides the desired corrective power to the intraocular lens so formed. Following injection of the medium, the interconnection between the insertion and injection device and the interior of the flexible bag is broken and a seal is formed so as to keep the medium within the flexible bag interior.

Preferably, the flexible bag is mounted upon a moveable member of the insertion and injection device. The moveable member is configured and arranged so that a distal end thereof acts on an interior surface of a distal end of the flexible bag when the moveable member is actuated to deploy the flexible bag. In this way, when a deployment force is applied to the moveable member it in turn applies a force to the distal end of the flexible bag causing the bag (e.g., successive portions of the bag) to be pulled or drawn out of the insertion and injection device aperture. In further embodiments, the insertion and injection device includes an outer member having a lumen in which lumen is disposed the flexible bag mounted upon the moveable member.

More particularly, the moveable member also is configured and arranged so as to include a lumen and one or more ports in fluid communication with the lumen. Further, the flexible bag is mounted upon the moveable member such that the one or more ports are in fluid communication with the interior of the flexible bag. In addition, the moveable member lumen is fluidly coupled to the source of injection medium.

In use, the insertion and injection device is manipulated by the surgeon or user so that a portion of the outer member is disposed within the eyes, the portion including the aperture from which the flexible bag is deployed. Following such insertion, the moveable member is actuated and the flexible bag is pulled or drawn out of the outer member until the flexible bag is fully deployed from the aperture. Following deployment, the insertion and injection device is actuated such that the medium is communicated from the source through the moveable member lumen, through the ports and thus into the interior of the flexible bag thereby inflating the flexible bag as hereinabove described.

Following inflation of the flexible bag to form the intraocular lens, the moveable member is again actuated so as to withdraw the moveable member from within the flexible bag. In more particular embodiments, the flexible bag is configured and arranged so as to include a self-sealing mechanism in which is received the moveable member when the flexible bag is mounted upon the moveable member. The self-sealing mechanism engages the outer surface of the moveable member so that a fluid seal is established between the flexible bag and the moveable member that essentially prevents the injected medium from leaking out of the interior of the flexible bag. The self-sealing mechanism also is configured and arranged in conjunction with the configuring and arranging of the moveable member such that the mechanism forms another fluid seal to prevent the injected medium from leaking out of the flexible bag after the moveable member is withdrawn from the flexible bag.

In yet further embodiments, the flexible bag is configured and arranged with one or more, more particularly a plurality, of haptics, loops or feet that extend outwardly from the flexible bag when it is deployed. The haptics are configured and arranged so as to support and fix the inflated flexible bag comprising the intraocular lens within the eye. The haptics are disposed within the insertion and injection device along with the flexible bag so as to prevent damage to the bag during storage and when the flexible bag is being deployed.

In one illustrative exemplary embodiment, the haptics are composed of shape memory material such as a super-elastic nitinol material such that the haptics are preformed so as to exhibit a desired configuration when deployed but which can be stored or packaged within the insertion and injection device in another configuration, for example a nearly straight configuration. In another illustrative exemplary embodiment, the haptic has a plate shaped configuration and can be made of the same material as the flexible bag.

Also featured is a method for deploying or inserting an introcular lens according to the present invention, methods for treating aphakia and kits including the insertion and injection device and/or the flexible bag.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character acter denote corresponding parts throughout the several views and wherein.

DESCRIPTION OF THE PREFERRED EMBODIMENT

Figure 1:
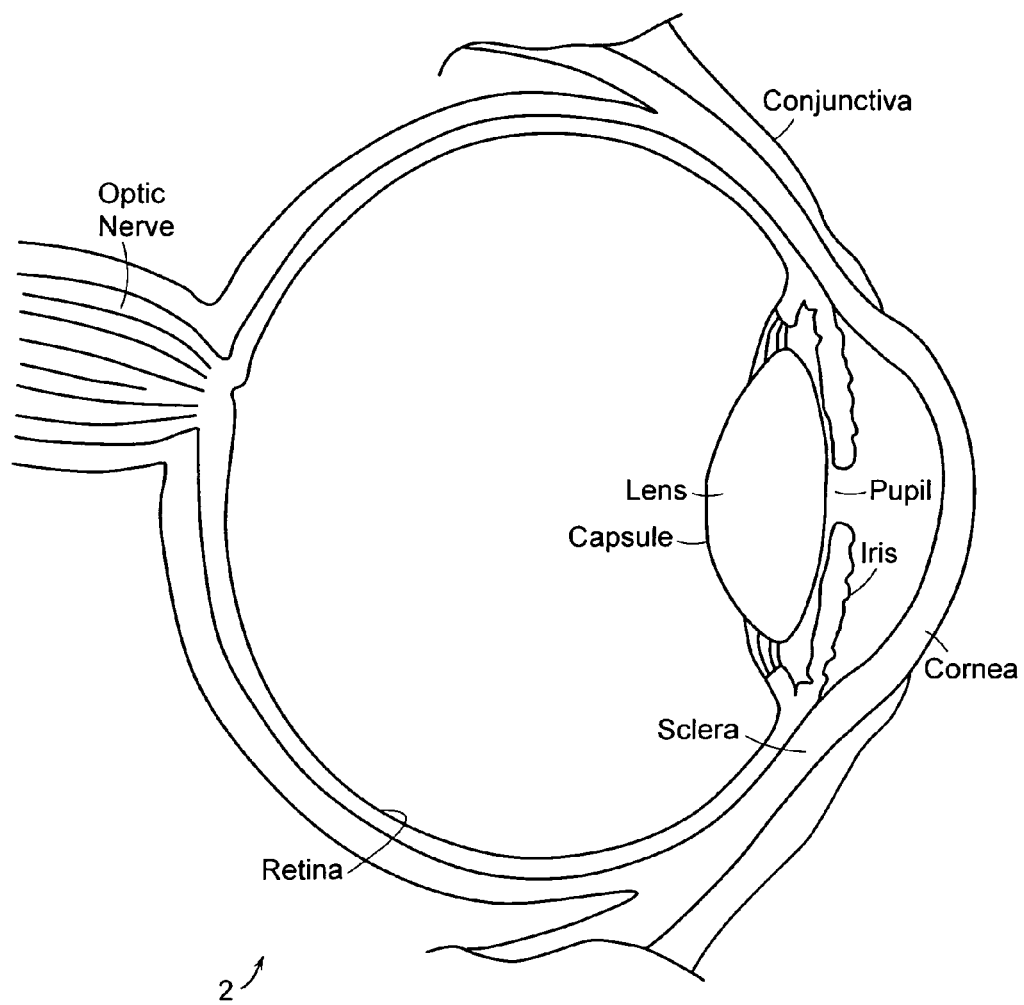
FIG. 1 is a cross-sectional schematic view of a non-diseased eye to illustrate basic components or structure of the human eye.
Figure 2:
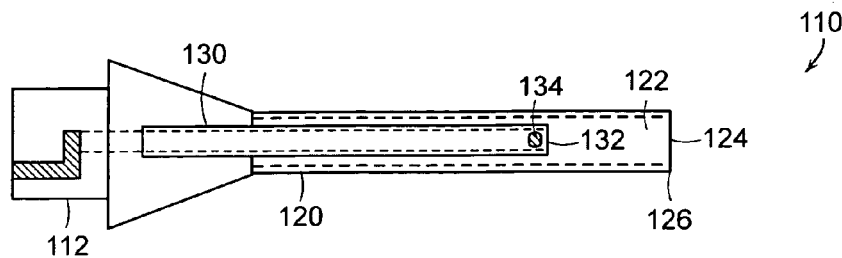
FIG. 2 is an illustrative top view of an intraocular lens insertion and injection device according to the present invention with the lens removed for clarity.

In the following discussion, reference shall be generally made to the illustrative cross-sectional view of an eye 2 provided in FIG. 1 for the general details and structure of the eye. Referring now to the various figures of the drawing wherein like reference characters refer to like parts, there is shown in FIGS. 2–4 various views of the injectable bag intraocular lens system 100 according to the present invention and/or elements of such a system including an insertion and injection device 110 and an intraocular lens 140.

Figure 4:
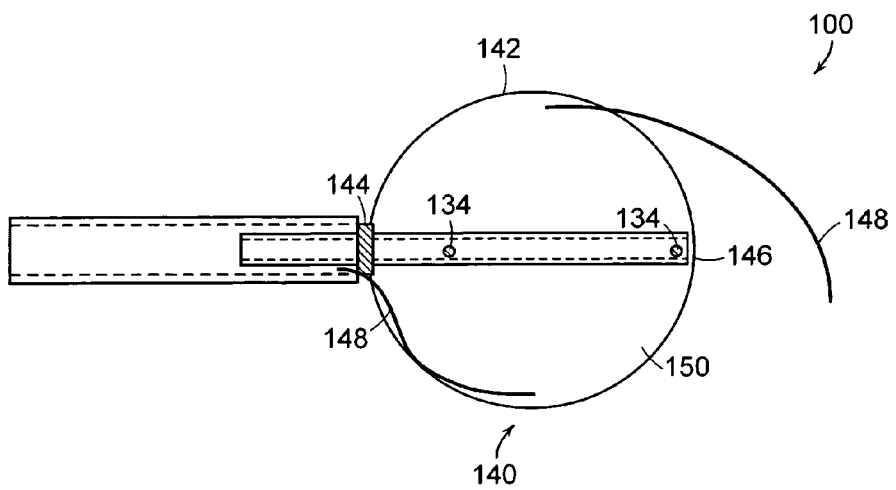
FIG. 4 is a top view of the intraocular lens insertion and injection device of FIGS. 2–3, illustrating the extension of the moveable member and the inflation of the lens.
Figure 5:
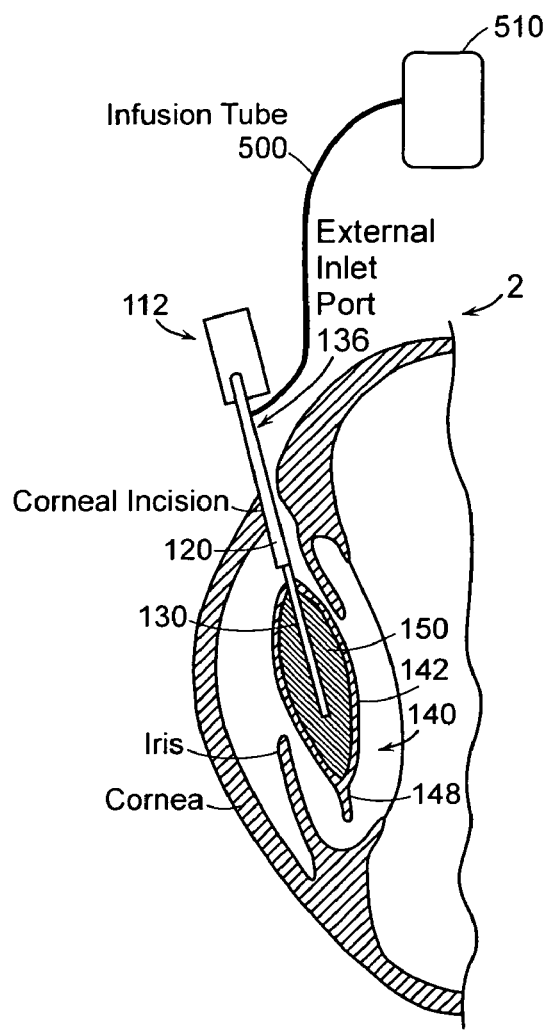
FIG. 5 is a cross-sectional view of an eye generally illustrating a part of the implantation process using the system and methodology of the present invention.

The insertion and injection device 110 includes an outer member 120 and an inner member or plunger member 130. The outer member 120 includes a lumen 122 and an aperture 124 in communication with the lumen. The plunger member 130 is movably disposed within the outer member lumen 122 so that it traverses along the length of the outer member lumen between a first position where the distal end 132 lies within the outer member end as shown in FIGS. 2–3 and a second position where the distal end 132 extends outwardly from the outer member aperture 124 as shown in FIGS. 4–5.

Figure 3:
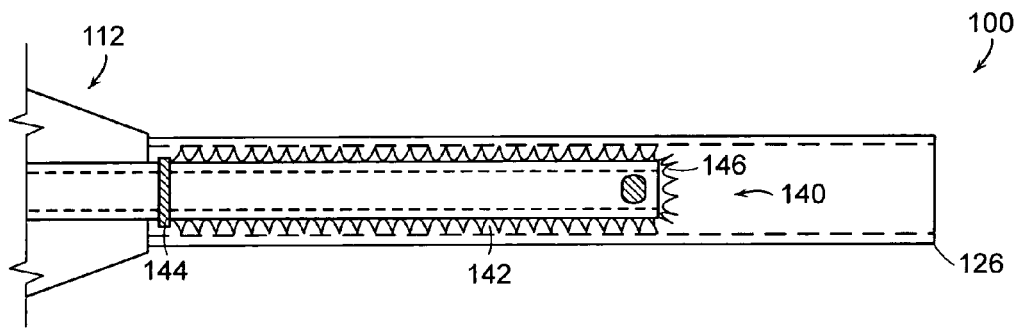
FIG. 3 is an partial view of the intraocular lens insertion and injection device of FIG. 2 to illustrate pre-insertion mounting of the lens on the moveable member.

The first position of the plunger member 130 generally corresponds to a storage position when the flexible bag 142 comprising the intraocular lens 140 is mounted on and about the plunger member as is more clearly shown in FIG. 3. In this configuration, the plunger member 130 passes through a self-sealing mechanism 144 of the flexible bag 142 such that the distal end 132 and the outlet or port 134 of the plunger member reside within the interior of the flexible bag. The flexible bag 142 also is preferably arranged about the plunger member 130 using any of a number of techniques known to those skilled in the art, including rolling and folding, so as to facilitate the deployment of the flexible bag from within the outer member 120. In more particular embodiments, the flexible bag 142 is arranged about the plunger member 130 so that the distal end 146 of the flexible bag is proximal the plunger member distal end 132.

The plunger member distal end 132 also is generally configured and arranged so that it should not pierce the flexible bag distal end 146 when the plunger member is being moved from the first to the second position. In more particular embodiments, the plunger member distal end 132 is a blunt or rounded end. The end shape and the thickness of the plunger member 132 also are preferably established so as to reduce the potential for damage to the bag self-sealing mechanism 144 when the plunger mechanism is received therein.

The second position of the plunger member 130 generally corresponds to a fully extended flexible bag position, the condition of the flexible bag 142 that is established so the bag can be inflated the desired amount by the injection of the medium 150 therein via the plunger member port(s) 134. The plunger member 130 is moved from the first to the second position by any of a number of mechanisms known to those skilled in the art which can cause the plunger member to be moved back and forth between the first and second positions including mechanisms or devices that are mechanically or fluidly coupled to the plunger member to cause such motion and which are hand-operated or motor operated. In an exemplary embodiment, a motorized screw-drive type of assembly provides the motive force for so moving the plunger member.

In the illustrated embodiment, the distal end 126 of the outer member 120 is shown as being a blunt end, however, this shall not constitute a limiatation. It is within the scope of the present invention for the outer member distal end 126 to have any of a number of end details known to those skilled in the art, including a sharp or tri-beveled end particularly configured for penetrating the cornea and/or conjunctiva of an eye instead of being passed through an incision in the cornea.

The plunger member 130 also shall include an external inlet port 136 that is configured and arranged so it can be interconnected to an infusion tube 500 from the external source 510 of the medium to be injected (see FIG. 5). The external inlet port, infusion tube and source shall be any of a number of devices, mechanism and/or containers known to those skilled in the art including for example a port configured so as to be a Leur-lock type of connection.

The insertion and injection device 110 also includes a handle member 112 that is arranged and configured so as to allow the member to be gripped by a surgeon or technician that is performing the surgical procedure. This, however, shall not constitute a limitation as it is within the scope of the present invention for the insertion and injection device 110 to be held by or secured to a member (not shown) of an automated arm assembly or a manually operated arm assembly, each controlling the motion of the intra-operative microsurgical device. In such cases, the arm assembly provides a mechanism to control movement of the insertion and injection device 110 or elements thereof along predetermined and position determinable paths. It also is within the scope of the present invention for this manually operated or automated arm assembly to further include a mechanism for controlling the movement of the plunger member between the first and second positions and also to control the injection of the medium.

The handle member 112 is constructed of any of a number of materials known to those skilled in the art that are appropriate for the intended use and structural loads imposed thereon during use. Such materials include metals such as stainless steel and plastics such as polymides. The outer member 120 and the plunger member 130 are constructed of any of a number of materials known to those skilled in the art that are appropriate for the intended use including metals such as stainless steel. Also, and although generally illustrated as being generally cylindrical in shape, the outer member 120 and the plunger member 130 can be configured so as to have any geometric shape otherwise consistent with the teachings and function of the present invention.

In illustrative embodiments, the outer member 120 is generally sized so as to be insertable through the incision made to extract the natural lens from the capsule of the lens, more particularly sized so as to have a diameter about 3 mm or less, and more specifically sized so as to have a diameter in the range of from about 2–3 mm, more preferably a diameter of about 2 mm. In an illustrative exemplary embodiment, the plunger member 130 is generally sized so as to have a diameter of about 1 mm.

The intraocular lens 140 is in the form of a flexible bag 142 made from a biocompatible optically clear material. The material making up the flexible bag and the wall thickness of the flexible bag are generally selected so that the loading imposed by the plunger member 130 should not perforate the flexible bag and so that the injection of the medium 150 also should not cause a perforation of the flexible bag. Correspondingly, the wall thickness should not be set so thick the bag loses its flexibility. In exemplary embodiments, the wall thickness of a clear polymeric material such as a silicone or polyurethane material would be not more than about 0.15 mm and more particularly in the range of from about 0.04 mm to 0.15 mm. Such materials and thickness are illustrative and thus are not considered limiting, as it is within the scope of the present invention for any of a number of bio-compatible materials known to those skilled in the art are contemplated for use with the intraocular lens according to the present invention.

The flexible bag 142 is generally sized so that when inflated it essentially fills and fits firmly within the lens capsule of the eye, typically the flexible bag when it is inflated will have a diameter on the order of about 5–6 mm. Also, the flexible bag 142 should be filled with the injected medium 148 so that the inflated flexible bag yields an intraocular lens having the same general shape as the biological lens material normally contained in the lens capsule but which has been removed for medical reasons, typically such a configuration or shape is commonly referred to as bi-convex.

As indicated above, the flexible bag 142 includes a self-sealing mechanism 144 as is known to those skilled in the art which sealing receives the plunger member 130 therein. The self-sealing mechanism 144 also sealingly engages the outer surfaces of the plunger member 144 so as to form a seal about the plunger member so the injected medium does not leak out passed this seal. Additionally, the self-sealing mechanism 144 preferably automatically closes itself when the plunger member 130 is withdrawn therefrom so that the injected medium also does not leak out from the interior of the inflated flexible bag 142. It is further desirable that the self-sealing mechanism be utilized at a later time to allow one to access the interior of the inflated flexible bag forming the implanted intraocular lens so that the amount of medium can be increased or decreased when needed to adjust the refractive power of the intraocular lens. Preferably such adjustment is accomplished with the need for making another surgical incision or accomplished by making a minimally-invasive incision. In an illustrative exemplary embodiment, the self-sealing mechanism 144 comprises a self-sealing valve or grommet more particularly the self sealing valve would be similar conceptually to the injection port in IV bottles or insulin delivery pumps.

The medium 150 injected into the flexible bag 142 is any of a number of essentially optically pure biocompatible materials known to those skilled in the art that can be relatively easily injected into the flexible bag 142 as herein described. In an exemplary embodiment, the medium 150 is a gas or a liquid although the medium preferably is a liquid because of the capability in most cases of achieving a desired refractive power using liquids as compared to gases. Suitable liquids for purposes of inflating include, but are not limited to, solutions of physiological salts, Dextran, polymeric material such as silastic, an aqueous saline solution, silicone oil, silicones, gelatins, polyvinyl alcohols as well as materials that are liquid or flowable in one state and will polymerize or gel to maintain its configuration under the environmental conditions extant within the eye such as that described in U.S. Pat. No. 4,693,707 the teachings of which are incorporated herein by reference.

Attached to ends of the flexible bag 142, for example opposing ends, there are secured haptics 148, loops or feet. In an exemplary illustrative embodiment, the haptics 148 are made from small gage Nitinol wire, a shape-memory material. The Nitinol haptics 148 preferably are pre-formed for a curved configuration, but are packaged in a nearly straight position inside the outer member 120 as hereinabove described. The superelastic properties of Nitinol allows it to conform to different configurations under an applied force, but return to its original configuration (without creep) in the absence of external forces. Alternatively, the haptic 148 is of a plate type of design, and as such uses the same material as the flexible bag 142.

The invention also includes device or system kits that comprise one or more insertion and injection devices 110 of the present invention including a pre-mounted flexible bag 142 also according to the present invention with or without the infusion tubing 500 and container 510 of the injected medium 150 that would be used to inflate the flexible bag so as to yield an intraocular lens 140 according to the present invention. In a specific embodiment, a device kit includes only an outer member 120 and a plunger member 130 and a pre-mounted flexible bag 142, forming in effect a one time use type of device kit that is combined with other elements of the system.

Figure 6:
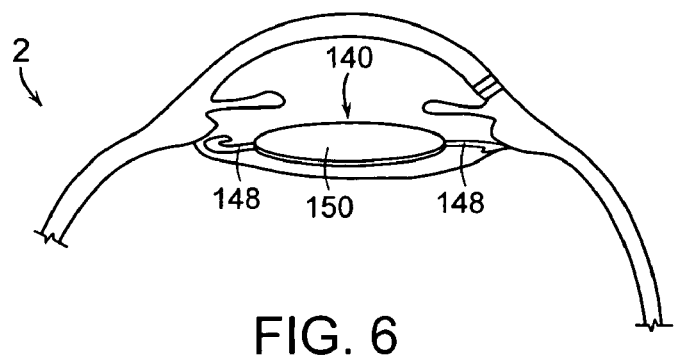
FIG. 6 is an illustrative cross-sectional view of the eye generally showing implantation of the lens using the methodology of the present invention.

The use of injectable bag intraocular lens system 100, the elements of this system and related methodologies of the present invention can be further understood from the following discussion concerning a method for treating a cataract and with reference to FIGS. 4–6. Reference also shall be made to FIGS. 2–3 for specific components or elements of the injectable intraocular lens systems 110 not otherwise shown in FIGS. 4–6 and to FIG. 1 for general structure of the eye 2.

In treating a cataract or aphakia, the natural lens of the impaired eye is removed using any of a number of techniques known to those skilled in the art including cryoextraction, extracapsular extraction or phaceoemulsification. In the phaceoemulsification technique, the capsule of the lens is pierced or breached on the anterior chamber side of the capsule. The capsule of the lens, capsule, or lens capsule is a transparent highly elastic and brittle membrane that closely surrounds the lens in the eye 2. An ultrasonic wave generating apparatus or device is inserted through an incision in the cornea to break-up the impaired lens and the broken up biological material is aspirated therefrom as is well known to those skilled in the art. Although the natural lens is removed, in this technique the lens capsule remains so as to maintain the barrier between the vitreous body and posterior chamber.

In preparation of implanting a intraocular lens 140, the infusion line 500 for medium injection is attached to the external inlet port 136 of the plunger member 130 so that at the appropriate time, the medium 150 can be injected through the plunger member into the flexible bag 142. Thereafter and following removal of the natural lens, the insertion and injection device 110 with a pre-mounted flexible bag 142, such as shown in FIG. 3, is manipulated manually, by a manually operated apparatus or by a motorized apparatus so that the outer member distal end 126 is inserted through the corneal incision and is placed within the eye 2. In an exemplary embodiment, the outer member distal end 126 is positioned so that it lies within the lens capsule.

Following such insertion of the outer member distal end 126 within the eye 2, the plunger member 130 is actuated so that the distal end 132 thereof advances through the outer member lumen 122 and thence out of the outer member aperture 124. As herein above-described, the plunger member distal end 132 acts on the inside surface of the flexible bag 142, the distal end 146 of the flexible bag, so that the advancement of the plunger member distal end beyond the outer member aperture 124 causes the flexible bag to be drawn or pulled out from within the outer member 120 thereby deploying the flexible bag within the eye. In the case where the outer member distal end 126 is disposed in the lens capsule, the advancement of the plunger member distal end 132 causes the flexible bag to be deployed into the lens capsule.

Following deployment of the flexible bag 142, the medium 150 is injected into the bag via the plunger member lumen and the one or more plunger member ports 134 and into the flexible bag so as to cause the inflation of the flexible bag. The amount of medium 150 that is injected into the flexible bag 142 will affect in some degree the curvature of the lens and thus the refractive power of the intraocular lens so formed. By this adjusting to precisely metered values or amounts of fluid, the refractive power of the lens can be adjusted to compensate.

After proper inflation of the flexible bag 142 thereby forming an intraocular lens having the desired refractive power characteristics, and in the case where the flexible bag is deployed in the eye, then insertion and injection device is manipulated, such as that shown in FIG. 5 so the intraocular lens formed by the properly inflated flexible bag is disposed in the lens capsule as is shown in FIG. 6. After so manipulating or in the case where the flexible bag was already deployed in the lens capsule prior to inflation, the plunger member 130 is again actuated but in a direction such that the plunger member distal end 132 is withdrawn from the flexible bag 142 past the self-sealing mechanism 144 and generally back within the confines of the outer member 120 as illustrated in FIG. 2.

Insertion or implantation of the intraocular lens 140 now being complete, the insertion and injection member 110, more particularly the outer member 120 and the plunger member 130, are pulled back out the incision and thus out of the eye 2. Thereafter, the surgeon or surgical personnel take what other action is appropriate for sealing or closing up any of the incisions made in the eye during the conduct of the cataract procedure.

The above-described system an methodology according to the present advantageously yields a system and method whereby a lens can be inserted using minimally sized incision holes in the eye while providing the capability to adjust the refractive power being developed by the implanted by appropriately selecting the amount and type of fluid being injected into the flexible bag. The above described system also advantageously simplifies the process by eliminating multiply component parts disclosed in prior art system that separately eject a deflated lens from the insertion device and separately inject the medium into the lens within the eye.

Although a preferred embodiment of the invention has been described using specific terms, such description is for illustrative purposes only, and it is to be understood that changes and variations may be made without departing from the spirit or scope of the following claims.

What is claimed is:

1. An intraocular lens system comprising an insertion and injection device and a deflated lens member having an interior;
   wherein the insertion and injection device includes;
   a moveable member having a outlet port provided therein,
   an outer member in which is disposed the moveable member,
   wherein the deflated lens member is mounted about and to an end of the moveable member such that the deflated lens member is sealingly engaged with a portion of the moveable member so that the interior of the deflated lens member forms a compartment,
   wherein the moveable member outlet communicates with the deflated member compartment, wherein the deflated lens member includes a self-sealing mechanism in which the insertion and injection device is removably and sealingly received such that the insertion and injection device can be removably and sealingly received in the self-sealing mechanism repeatedly, and wherein the self-sealing mechanism is flush or continuous with the surrounding lens member.

2. The intraocular lens system of claim 1, wherein the moveable member and the deflated lens member mounted thereon are movably disposed within the outer member such that the moveable member is movable between a first position and a second position, the second position corresponding to a deployed condition of the deflated lens member external to the outer member.

3. The intraocular lens system of claim 2, wherein a distal end of the moveable member is configured and arranged so as to engage an interior surface of the deflated lens member whereby the deflated lens member is drawn out from the outer member when the moveable member is moved from the first position to the second position.

4. The intraocular lens system a claim 1, further comprising a source of an optical medium, the source being operably coupled to the insertion and injection device such that when the moveable member is in the second position, the optical medium is injected into the deflated lens member compartment via the moveable member outlet port.

5. The intraocular lens system of claim 4, wherein the moveable member includes a plurality of outlet ports.

6. The intraocular lens system of claim 1, wherein the moveable member includes a plurality of outlet ports.

7. The intraocular lens system of claim 1, wherein the deflated lens member includes a self-sealing mechanism which is removably and sealingly received by the moveable member.

8. The intraocular lens system of claim 1, further comprising one or more haptics extending outwardly from the deflated lens member.

9. An intraocular lens system comprising an insertion and injection device and a deflated lens member having an interior;
   wherein the insertion and injection device comprises an outlet member, the deflated lens member is mounted to the outlet member, wherein the deflated lens member includes a self-sealing mechanism in which the insertion and injection device is removably and sealingly received such that the insertion and injection device can be removably and sealingly received in the self-sealing mechanism repeatedly and wherein the self-sealing mechanism is flush or continuous with the surrounding lens member.

10. A method for implanting an intraocular lens in an eye and adjusting refractive power of the intraocular lens at any time following implantation comprising:

mounting a deflated lens member about and to an end of a moveable member such that the deflated lens member is sealingly engaged with a portion of the moveable member via a self-sealing mechanism so that an interior of the deflated lens member forms a compartment and such that on outlet port in the moveable member communicates with the deflated member compartment;

disposing an outer member about the moveable member;

inserting a portion of the outer member within the eye via an incision;

moving the moveable member from a first position within the outer member to a second position outside of the outer member, thereby deploying the deflated lens member;

forming the intraocular lens by injecting an optical medium into the deflated lens member compartment when the moveable member is in the second position using the moveable member outlet port;

moving the movable member from the second position outside the outer member to the first position within the outer member while the movable member concurrently withdraws out of the lens member thereby implanting the lens within the eye;

allowing the self-sealing mechanism to seal the lens;

removing the movable member from the eye and allowing the intraocular lens to remain in the eye;

closing the incision; and adjusting the refractive power of the intraocular lens at any time after the movable member is removed from the eye and the intraocular lens remains in the eye, by inserting an injection device into the intraocular lens to adjust the amount of optical medium in the intraocular lens.

11. The method for implanting an intraocular lens according to claim 10, wherein said forming an intraocular lens further includes injecting a pre-determined amount of die optical medium into the deflated lens member compartment so as to selectively control the refractive power of the formed intraocular lens.

12. The method for implanting an intraocular lens according to claim 10, wherein while moving the moveable member to the second position, said moveable member acts on an interior surface of a distal end of the deflated lens member so as to cause the distal end to be first withdrawn from within the outer member.

13. The method for implanting an intraocular lens according to claim 12, wherein portions of the deflated lens member are successively withdrawn from the outer member by said moveable member acting.

14. The method for implanting an intraocular lens according to claim 10, further comprising moving the moveable member from the second position towards the first position after injecting the optical medium so as to withdraw the moveable member from the inflated lens member.

15. A method for treating one of aphakia or cataract of an affected eye, comprising:

removing the impaired natural lens of the affected eye;

mounting a deflated lens member about and to an end of a moveable member such that the deflated lens member is sealingly engaged with a portion of the moveable member so that an interior of the deflated lens member forms a compartment and such that an outlet port in the moveable member communicates with the deflated member compartment;

disposing an outer member about the moveable member;

inserting a portion of the outer member within the eye;

moving the moveable member from a first position to a second position, thereby deploying the deflated lens member;

forming an intraocular lens by injecting an optical medium into the deflated lens member compartment when the moveable member is in the second position using the moveable member outlet port;

removing the movable member from the eye; and allowing the intraocular lens to remain in the eye, wherein the lens member includes a self-sealing mechanism that is flush or continuous with the surrounding lens member, wherein the movable member is removably and sealingly received in the self-sealing mechanism and wherein after the movable member is removed from the eye and the intraocular lens remains in the eye, an injection device is inserted into the self-sealing mechanism to adjust the amount of optical medium in the intraocular lens.

16. The method for treating according to claim 15, wherein said forming an intraocular lens further includes injecting a pre-determined amount of the optical medium into the deflated lens member compartment so as to selectively control the refractive power of the formed intraocular lens.

17. The method for treating according to claim 15, wherein while moving the moveable member to the second position, said moveable member acts on an interior surface of a distal end of the deflated lens member so as to cause the distal end to be first withdrawn from within the outer member.

18. The method for treating according to claim 17, wherein portions of the deflated lens member are successively withdrawn from the outer member by said moveable member acting.

19. The method for treating according to claim 15, further comprising moving the moveable member from the second position towards the first position after injecting the optical medium so as to withdraw the moveable member from the inflated lens member.

20. A device kit comprising at least one insertion and injection device and a deflated lens member having an interior;

wherein the insertion and injection device includes:

a moveable member having a outlet port provided therein, an outer member in which is disposed the moveable member, wherein the deflated lens member is mounted about and to an end of the moveable member such that the deflated lens member is sealingly engaged with a portion of the moveable member so that the interior of the deflated lens member forms a compartment, and wherein the moveable member outlet communicates with the deflated member compartment through a self-sealing mechanism in which the movable member is removably and sealingly received and wherein the self-sealing mechanism is flush or continuous with the surrounding lens member.

21. A method for treating one of aphakia or cataract of an affected eye, comprising:

removing the impaired natural lens of the affected eye;

mounting a deflated lens member, having an interior compartment, about the end of a moveable member via a self-sealing mechanism in the deflated lens member such that an outlet port in the moveable member communicates with the interior compartment of the deflated member;

disposing an outer member about the moveable member;

inserting a portion of the outer member within the eye;

moving the moveable member from a first position within the outer member to a second position outside of the outer member, thereby deploying the deflated lens member;

forming on intraocular lens by injecting an optical medium into the deflated lens member compartment when the moveable member is in the second position using the moveable member outlet port;

moving the moveable member from the second position outside of the outer member to the first position within the outer member while the movable member concurrently withdraws out of the self-seating mechanism of the lens member;

removing the outer member from the eye;

allowing the intraocular lens to remain in the eye;

closing any incisions made in the eye during treatment;

subsequently inserting an injection device into the intraocular lens via the self-sealing mechanism; and adjusting the amount of optical medium in the intraocular lens by injecting additional optical medium into the lens and/or removing optical medium from the lens.

* * * * *